United States Patent [19]
Smith

[11] Patent Number: 6,024,449
[45] Date of Patent: Feb. 15, 2000

[54] HIGH SPEED TOPOGRAPHY MEASUREMENT OF SEMI-DIFFUSE OBJECTS

[76] Inventor: Robert F. Smith, 3714 Henley Dr., Pittsburgh, Pa. 15235

[21] Appl. No.: 09/113,028

[22] Filed: Jul. 13, 1998

[51] Int. Cl.[7] ........................................ A61B 3/10
[52] U.S. Cl. ............................ 351/212; 356/376
[58] Field of Search .................... 351/205, 211, 351/212; 606/12, 5, 108; 356/376

[56] References Cited

U.S. PATENT DOCUMENTS

| | | | |
|---|---|---|---|
| 4,995,716 | 2/1991 | Warnicki et al. | 351/212 |
| 5,350,374 | 9/1994 | Smith | 606/5 |
| 5,406,342 | 4/1995 | Jongsma | 351/212 |
| 5,624,437 | 4/1997 | Freeman et al. | 606/12 |
| 5,645,550 | 7/1997 | Hohla | 606/108 |
| 5,782,822 | 7/1998 | Telfair et al. | 606/5 |

*Primary Examiner*—George Manuel

[57] ABSTRACT

Forming an image on a CCD of a grid pattern projected on a target surface and detecting the positional coordinates of the image by correlating voltage peaks in the CCD output voltage during pixel readout synchronized with the count of pulses from a master clock. Topography is calculated by knowing the equations of the rays comprising the projection pattern and the rays from the determined CCD positional coordinates and solving for the 3D coordinates formed by the intersections of the two sets of rays. Means are provided for: blocking the specular component of reflected light from the target surface while passing the diffuse component; forming the rays of the projected grid pattern so that fluctuations in the target surface position do not cause measurement error; adequate focussing of the full grid pattern on the CCD; differentiating the CCD output voltage and detecting a zero crossing for precise timing of count capture at the instant of a peak. In a preferred embodiment, the target surface is a cornea undergoing PRK and a laser projection source pulsed at a high enough rate to provide real time differential topographical display and feedback to the photoablation means. Alternate embodiments include: using the uv photoablating laser as also the projection source in conjunction with a uv sensitive CCD; an adjunct CCD type sensor in the 8 micron region for monitoring corneal sector temperatures during PRK concurrent with the topography measurement.

20 Claims, 9 Drawing Sheets

HIGH SPEED TOPOGRAPHY MEASUREMENT OF SEMI-DIFFUSE OBJECTS

BACKGROUND OF THE INVENTION

The patents of Jongsma (U.S. Pat. No. 5,406,342), Warnicke, et al.(U.S. Pat. No. 4,995,716) and Baron (U.S. Pat. No. 4,761,071), present inventions for systems and methods of projecting image patterns onto the cornea of the eye and then by means of a video camera, measure the shifting of elements of the image pattern and from the measurements compute the three dimensional surface topography.

Jongsma utilizes a frequency domain concept called "Fourier Profilometry" which has been implemented by Euclid Systems and, like the direct geometrical approach of the Warnicke invention implemented by Par Technology, employs the technique of rastostereography wherein a pattern is flash projected on the full surface of the anterior cornea to which a fluorescein dye has been applied. Because the light from the flash lamp is filtered to pass light only in the blue/violet wavelength region, the fluorescein dye causes the projected light to fluoresce to the wavelength of yellow light. Then a narrow bandpass filter allows only the diffuse reflected yellow light from the projected raster (or grid) image to reach the video camera. This prevents the blue/violet light reflected from the optically smooth surface, known as the specular surface, of the cornea from interfering with the imaging of the desired diffuse projected grid.

The two systems are in prominent usage and achieve topography measurement accuracies on the order of a few microns. Although both have been mentioned in the application of measuring corneal topography during photorefractive keratectomy, the problem of specular reflection has not been addressed in detail. For these systems to be used on surfaces such as would be encountered during the process of corneal photoablation where the epithelium has been removed to expose the stromal layer, no fluorescein dye is used and the light filters are removed. The problem that arises in this application is that unless the corneal surface totally diffuses the light (similar to a movie projection screen or a mat finish paper) remanent regular or specular reflected light from the semi-diffuse corneal surface can occlude portions of the diffuse image pattern when it is captured by the video camera.

Contemporary applications of these two systems, also to Placido disk type systems, are almost exclusively limited to single measurements of corneal topography for the purpose of ophthalmologic evaluation and/or contact lens fitting. Therefore, the several seconds they require to perform a topographic measurement is adequately rapid. However, for application to corneal surgery for refractive correction or therapeutic procedures, a real time, nearly continuous, topographic display is either necessary or desirable. The objective of such a system would be to provide to the ophthalmic surgeon a differential surface of the cornea showing micron level departures from the reference surface at frame rate indistinguishable from real time. Such performance was contemplated in my U.S. Pat. No. 5,350,374, but was limited in that it did not address the need to correct the specular reflected light problem and also was susceptible to errors caused by saccadic eye movement.

To create a system and method enabling real time topography measurement of semi-diffuse surfaces, the following objectives must be achieved: Preventing specular reflected light from interfering with the diffuse reflected light of the projected grid image; maximizing the light gathering power, the depth of field focussing capability, the resolving power and the image capturing speed of the video camera imaging system; minimizing the effect on measurement accuracy due to variations in the target object distance from the video camera; overcoming computational speed limitations of the prior art so that many full surface topographic measurements may be made per second.

SUMMARY OF THE INVENTION

The present invention is a system and method for making multiple full surface topographic measurements every second of a semi-diffuse target surface such as the de-epithelialized cornea of the eye undergoing photo refractive keratectomy (PRK) or photo therapeutic keratectomy (PTK). The system comprises a source of pulsed monochromatic polarized light for projecting a grid pattern comprised of bright lines, stripes or points onto the target surface. A video camera consisting of polarizing filter, objective lens, field correcting lens and CCD, attenuates the specular reflected components of light, and images the diffuse light from the grid pattern. A master clock governs the rate at which pixels of the CCD are readout in the form of an output voltage proportional to pixel light intensity. The pulses out of the master clock are counted by a master clock counter (MCC) which is set to zero at the beginning of each raster frame readout. Then by correlating peaks in the output voltage with MCC count values, the coordinate positions of the imaged grid pattern on the CCD can be determined on the fly, rather than first sequentially digitizing the CCD output voltage of each pixel, transferring the raster frame of pixels to computer memory and then interpolating among the matrix of pixel amplitude values to locate the position of peak pixel intensity as is the method used in prior art. Finally, because the spatial equations of the rays producing the projected grid pattern are known as are the rays through the video camera producing the image on the CCD, applying the techniques of analytical solid geometry yield the set of three dimensional coordinates constituting the topography of the target surface.

Another novelty of the present invention is the way the peak intensities of the grid pattern image are located to within a fraction of a CCD pixel without the need for computer interpolation and matrix manipulation. Interpolation is automatically performed by capturing the value of a master clock counter at the instant a peak—above a preset threshold—is detected in the CCD output; then because the master clock frequency is an order of magnitude times higher than the frequency at which the CCD pixels are readout, the effective position resolution is similarly multiplied.

A further novelty involves a means and method whereby the projected light grid pattern comprises a divergent group of rays whose effective origin, relative to the optical axis of the video camera, corresponds to the center of the video camera objective lens. By this means the target surface can fluctuate in position relative to the projection system and video camera frame of reference without materially affecting the accuracy of the topography measurement. This technique also simplifies the procedure for determining the positions of the light intensity peaks of the grid imaged on the CCD by aligning the horizontal rows and vertical columns of grid image points with the horizontal and vertical pixels, respectively, of the CCD and aligning the central ray of the projection system with the optical axis of the video camera.

In a preferred embodiment of the present invention, the target surface is the cornea of the human eye thereby requiring a grid pattern of about 8 mm diameter to encompass the optically useful portion of the cornea. The light projection source is a solid state pulsed laser producing plane polarized light, its narrow beam being expanded by a concave lens to produce a diverging cone of light of which is then captured by an aspherical converging lens, passed through a mask having vertical slits, then converged to another concave lens whose function is to diverge the image pattern of vertical lines in accord with the aforementioned method of eliminating topography errors due to variations in the cornea to video camera spacing. The effective mask slit spacing projected on the cornea is 0.2 mm and the width of the projected vertical lines is 0.075 mm—these values chosen to maximize the surface topography resolution as constrained by diffraction effects. The absence of chromatic aberration allows a single biconvex lens having an aspherical front surface to be used as the primary imaging means of the video camera. For purposes of sharply focussing all portions of the grid pattern projected on the full range of curvature variations of the human cornea, another lens is employed having an aspheric concave front surface and a planar back surface essentially in contact with the CCD. By mounting the projection system and video camera together on a movable platform and automatically controlling the position of the platform in the direction of the corneal target surface, a properly focussed grid pattern imaged can always be maintained. With regard to the selection of the CCD, a high sensitivity, back illuminated type 10 mm square with 1024×1024 pixels permits, in conjunction with the pulsed laser and high speed shuttering action, a means of insuring that saccadic eye motion does not degrade the accuracy of the topography measurement; further, the back illuminated CCD captures about all of the light to maintain high positional resolution of light intensity peaks. Then using a master clock frequency 16 times the pixel readout frequency permits a topography measurement accuracy of about plus or minus 0.001 mm. Also, as discussed above, a diverging ray projection method is to prevent variation in corneal positions from degrading the accuracy of topographic measurements.

Among the applications of the preferred embodiment of the present invention are those discussed in the prior art of U.S. Pat. No. 5,350,374: Enabling a means for feedback control of a laser ablation system; enabling the real-time viewing of the surface of the cornea relative to a reference spherical/ellipsoidal surface thereby also permitting manual control of the photoablation process. Because of the large number of photoablating laser delivery systems and techniques presently being used or investigated, the present invention allows quantitative evaluation of their efficacy both during and immediately after the corneal ablation procedure.

An alternate embodiment displaces the existing projection light source by the ultraviolet light from the photoablation device such as a 193 nm excimer laser whose beam already has the required cross section, needing only a diverging lens and some attenuation and a mask to form the requisite grid pattern. An advantage of such a system is the reduction of diffraction effects by a factor of about 3 to 1—relative to visible light—using an ultraviolet sensitive CCD and ultraviolet transmissive video camera optics. In a variation of this embodiment, the presence of fluorescing substances contained in the target object—such as potassium salts-can be utilized to fluoresce the laser radiation to produce the desired grid projection image in visible light.

An adjunct embodiment of the application to corneal topography in the course of corneal ablation is the use of a second CCD sensitive only in the infrared light region: By a process of beam splitting using a heat reflecting glass and infrared filter, the infrared CCD may be synchronized to the main topography determining CCD so that the corneal surface temperature may be measured within the specified 0.2 mm squares.

In addition to corneal topography, the invention contemplates application to the monitoring and feedback control of ablating a wide variety of objects; also in assembly lines where manufactured articles having semi-diffuse surfaces could be topographically measured to within a few microns at rates approaching several dozen articles per second. For articles having a smooth (specular) surface, such articles could first be cooled to cause moisture to deposit on their surfaces in the form of a microscopic fog that would create a sufficiently diffuse surface for topographic measurement.

DETAILED DESCRIPTION OF THE INVENTION

Figure 1:
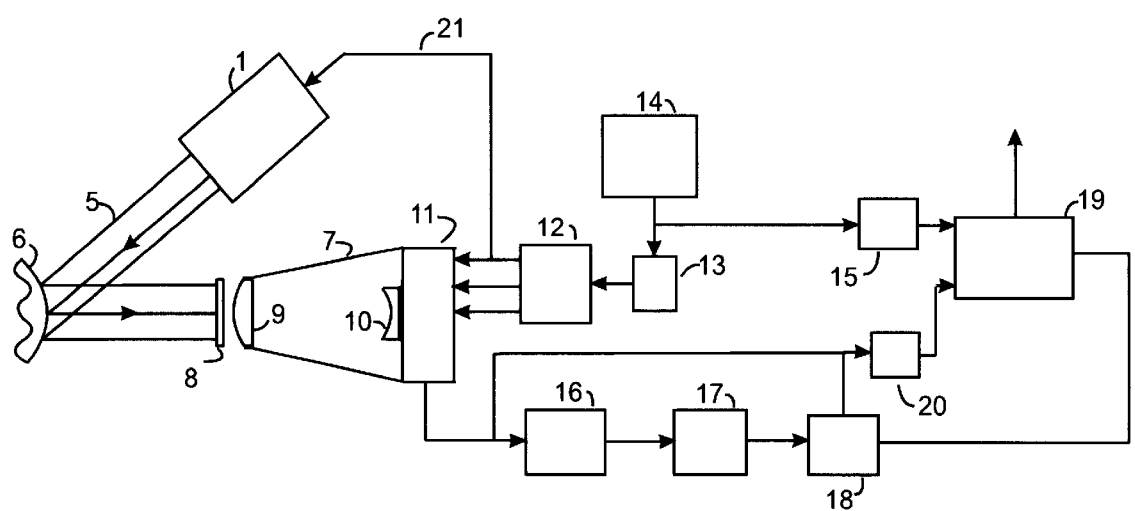
FIG. 1 is a diagram showing the essential elements of the present invention.

The basic functionality of the invention is illustrated in FIG. 1. A projection system 1 consists of a pulsed source of light that produces a substantially collimated uniform intensity beam of plane polarized light whose cross section is modulated in order to create a multitude of projection rays 5 that project a grid pattern on a target surface 6. The light from the grid pattern that is reflected from the target 6 is composed of two different components: The first is the light from the diffuse projected image which is the image that appears when a beam of light is directed at a diffusely reflecting surface—the apparent luminosity of such a viewed image remains substantially constant regardless of the angle from which it is viewed, such examples being a plastered wall or a movie projection screen. The second component of reflected light, called the regular or specular reflection, results when there is some remanent sheen or gloss to the surface so that the components of the incident beam obey the law of reflection subject to the average curvature of the surface. Such specular reflection, when it coincides with the rays from the diffuse reflection, is usually so intense that it obscures the desired diffuse projected image thereby defeating the topographic measurement technique. Therefore a means for sufficiently attenuating the specular image is necessary.

Because the diffuse light reflected from the target surface 6 is negligibly polarized, passing the image of the grid pattern through a plane polarizing filter rotated at right angles with respect to the axis of polarization of the projection system light source results in little attenuation of the diffuse component but significant attenuation of the specular component. It is by this means that the diffuse light component can be imaged on the CCD with minimal interference from the specular reflected image.

The video camera 7 is comprised of three components: A polarizing filter 8, an imaging/objective lens 9, a field flattening lens 10 and the CCD 11. The competing requirements for the video camera 7 of adequate light gathering power and depth of field place higher demands on the optical design than normally encountered in video camera design. One of the consequences is the need for the lens 10, the specific purpose of which is to provide uniform focussing across the face of the CCD 11 for the particular target surface selected. Further, by placing the optical axis which is also the Z axis, of the video camera 7 essentially on the optical axis of the target surface 6, the task of uniform focussing of all the light points of the grid image is made easier. If, however, the requirements of the application demand displacing the optical axis of the video camera from the Z axis, it is possible to compensate for the asymmetry of focussing on the target surface by means of tilting the CCD 11 so that it is not normal to the optical axis. The assumption implicit in the construction of the system is that all the elements are fixed in position with respect to each other with the exception of the target surface 6.

The remainder of the system consists of the data acquisition and topography computation portion of the invention. At the heart of the system is the master clock 14 which generates timing pulses having a small pulse-to-pulse time variation—i.e. a jitter on the order of 1 nanosecond. The master clock 14 frequency is intended to be adjustable so that the image frames per second can be varied. These pulses are directed to two locations: One of these locations is a frequency divider 13, which typically outputs one pulse for a fixed multiple of pulses out of 14; these lower frequency pulses out of 13 are then inputted into the CCD driver 12 which outputs horizontal and vertical transfer clock pulses to control the progressive row-by-row readout of the cells of the CCD; normally each pulse out of 13 will correspond to the readout of one pixel along a row of the CCD. Among other controlling signals to the CCD is an electronic shutter control signal 21 which also is used to synchronize the light pulses out of the light source 1. The other location to which the master clock 14 pulses are directed is the master clock counter (MCC) 15: It is by means of the MCC 15 that the essential principal of the invention obtains, i.e. there is a direct correlation between the count value of MCC 15 and the pixel position on CCD 11 so that at the instant a CCD output voltage peak is detected, the position of the associated light intensity peak is precisely defined. Employing time differentiation of the CCD output voltage provides a means for locating this peak to within a fraction of a pixel: As the CCD output voltage rises in the vicinity of pixels corresponding to light intensity maxima, the output voltage of the differentiator 16 increases in the positive direction; then near the very peak, the voltage drops, eventually passing rapidly through zero to a negative value. Next, the zero crossing detector 17 accurately detects the instant of this positive to negative transition in voltage and outputs a pulse which, together with the CCD output voltage is inputted to the gate circuit 18. If the CCD output voltage exceeds a predetermined threshold value, the pulse is transmitted through the gate circuit 18 to the digital register 19 causing the capture of both the MCC 15 value and the digitized value of the CCD output voltage formed by the analog to digital converter.

Figure 2:
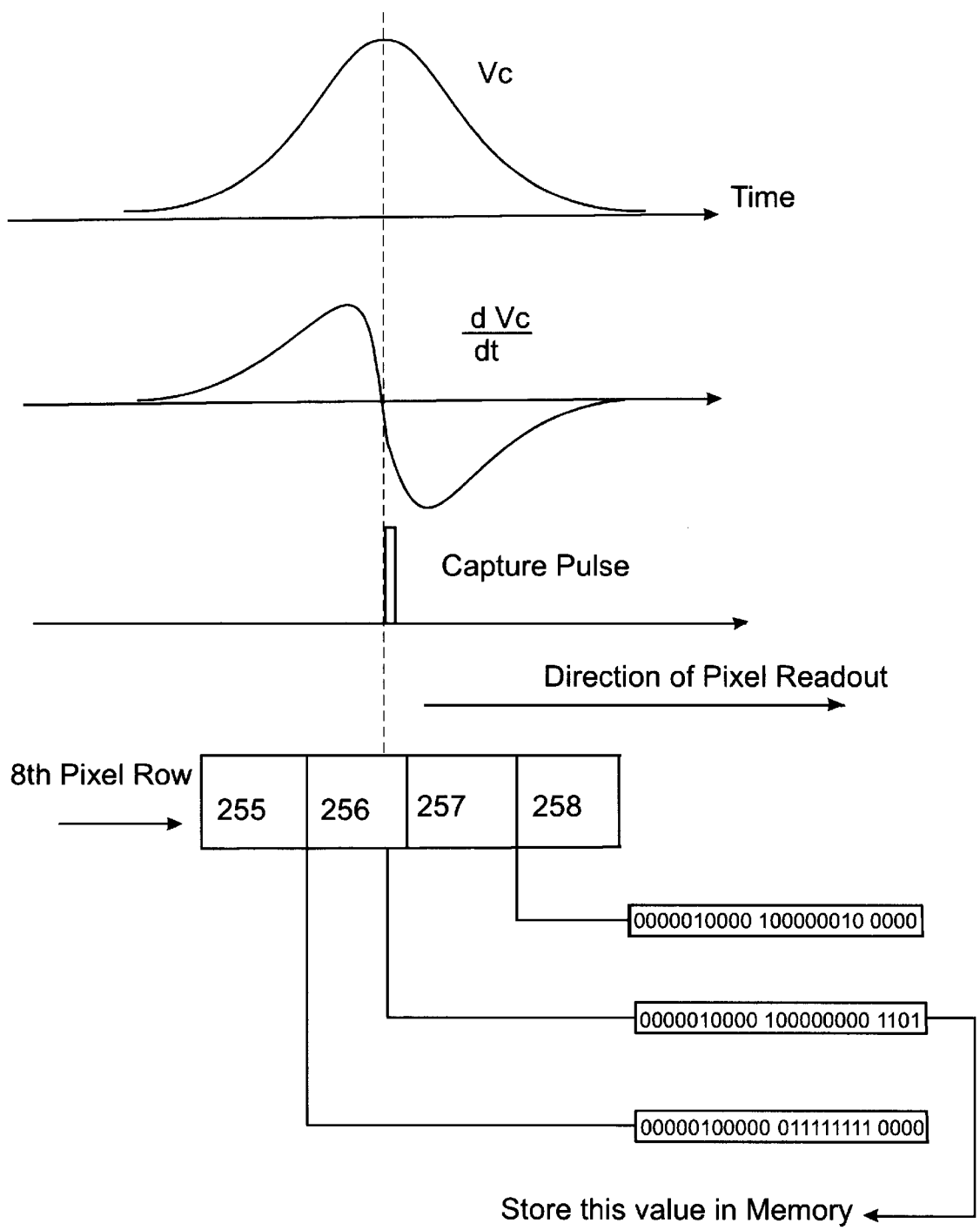
FIG. 2 is an illustration of the technique for peak intensity detection and time versus position correlation of the present invention

FIG. 2 illustrates the basic operation: The waveforms are plotted versus time showing respectively Vc (CCD output voltage), the time derivative of Vc, namely dVc/dt, and the pulse (output of block 17) which causes the capture of the pulse count of MCC 15 The vertical dashed line shows the behavior at the instant of a peak in Vc and also correlates to the readout of a row of pixels. For this illustration, it is assumed that there are 16 master clock pulses for each pixel readout and that there is a total of 511 pixels in each CCD row and also each master clock pulse increments the indicated binary register/word by one. As indicated in FIG. 2 the Vc peak occurs during the readout of the 256th pixel in the eighth row. Because the peak occurs 8 tenths through the interval of a single pixel readout, the master clock has outputted 13 pulses since the beginning of the pixel readout, causing a binary difference of 1101 in the least significant bits of the binary word. Thus the position of the light intensity peak on the CCD is obtained by reading the row value (000001000) in the uppermost 9 bits, the column value (pixel number in the row) is contained in the next 9 bits (100000000), and the fractional pixel by the last 4 bits (1101). These last 4 bits can be thought of as vernier scale for interpolating between pixels. It is noted that there is an inherent time delay between the time the master clock issues a pulse corresponding to an intensity peak and the time that the voltage peak readout of the CCD, Vc, is detected by the zero crossing detector. Because this time delay is constant, the MCC value can easily be compensated to exactly correlate count to position by a calibrating factor; the calibrating factor will vary depending on the number of frames captured per second. Also because distortions may exist in both the video camera optics and the grid pattern from the projection system 1, a matrix of correction factors can be used to preprocess the MCC values data to correct for these inaccuracies.

Figure 3:
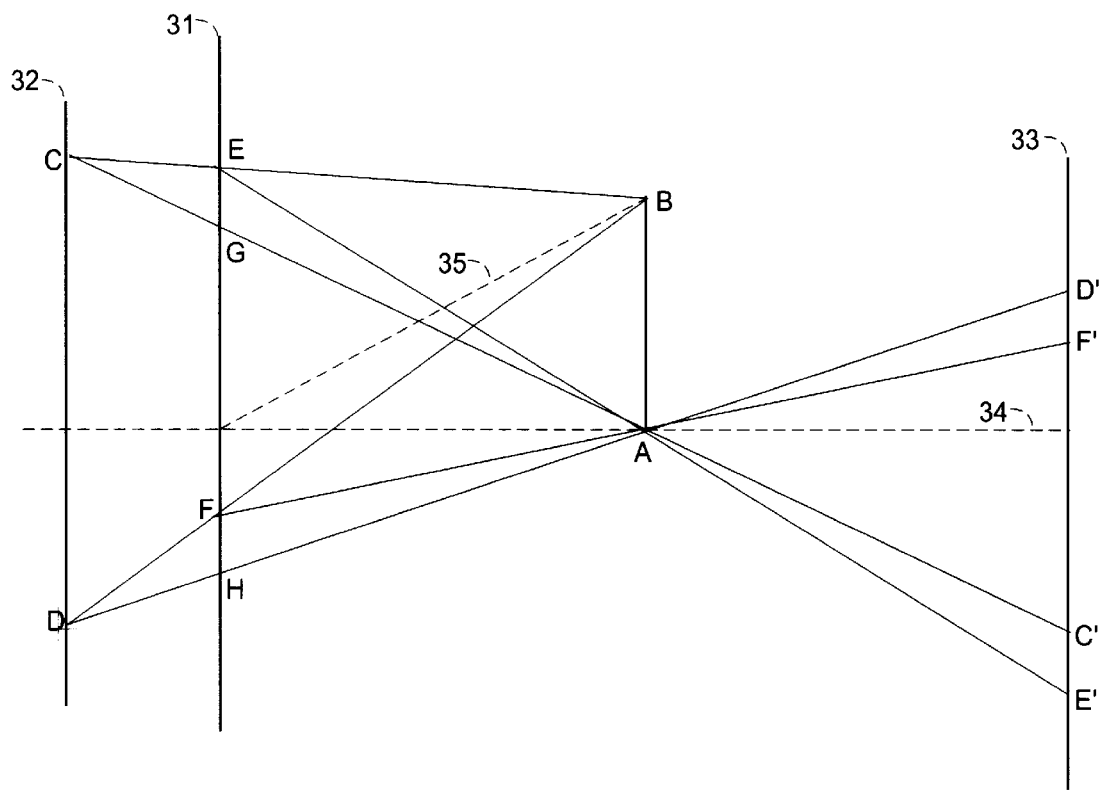
FIG. 3 depicts the geometrical method for eliminating topographical inaccuracies due to variations in distance between the measured surface and the measurement system.

An important parameter affecting topography measurement accuracy concerns the distance along the optical axis between the target surface and the objective lens 9 of video camera 7. If the grid pattern on the target surface 6 is formed by a perfectly collimated beam from the projection system 1, then the size of the grid pattern projected on the target surface does not change when the target surface distance changes; however, the size of the grid pattern imaged on the CCD will vary for fixed focus optics, so if the target surface distance is not accurately known beforehand, the topography of the target surface cannot be accurately calculated. A means was therefore sought to permit arbitrary fluctuations in target surface distance without affecting the accuracy of the topography measurement. To achieve this goal, the collimated projection rays 5 are modified so that, rather than being mutually parallel, they appear to emerge from a focal point located at the same distance from the apex of the target surface as the center of the objective lens 9. FIG. 3 illustrates the principles involved: A flat surface 31 is taken to be the initial position of the target surface; this surface is then moved to a new axial position 32. The axis of the projection system 35 intersects the axis of the optical system 34 at the surface 31. Two rays of the projection system emanate from point B, intersecting the initial plane position at E and F, and intersecting the final plane position at C and D. Then taking the center of the objective lens 9 as point A, the imaged points on the plane 33 are E', F' and C', D'. Now, the triangles ABC and ABD share a common side viz. AB. Because of the proportionalities involved, EG=FH and E'F'=C'D', showing that the imaged distance between the two projected rays on the target surface is geometrically invariant for any value of Z1. Further, F'D'=E'C', illustrative of the fact that all the points of the grid pattern imaged at projection plane 31 are shifted by a distance FADS for the pattern imaged at projection plane 32. If the distance AB=0, then no shifting occurs on the x axis of the image; this situation exists when the axis (or the central ray) of the projection system lies in the same horizontal plane as the optical axis of the video camera and thereby predefines the vertical positions of all the intensity peaks imaged on the CCD.

With the preprocessing of MCC values and the definition of the projection system rays, the calculation of the topography of the target surface proceeds as follows: Assigning the subscript o to the coordinates for the projected rays, the subscript c for the coordinates of the image on the CCD, and the subscript i for the coordinates of intersection of the projected rays and the rays from the CCD image points through the center of the video camera objective lens 9, then by the application of analytical solid geometry principles, the following equations result:

$$x_i = (z_c - z_o - R_{czx}x_c + R_{ozx}x_o)/(R_{ozx} - R_{czx})$$

$$z_i = (x_i - x_o)R_{ozx} - Zp, \text{ (elevation at } x_i, y_i)$$

$$y_i = y_o - z_i * DC_y / DC_z$$

$$R_{ozx} = DC_z / DC_x; R_{czx} = -Z1/x_c,$$

where: $DC_z$, $DC_y$, and $DC_x$ are the z, y and x direction cosines of the projection rays; Zp is the nominal distance (on the z optical axis) between the apex of the target surface and the source (focal point) of the projection rays; Z1 is the nominal distance between the apex of the target surface and the center of the objective lens.

An advantage afforded by this geometrical technique is that, when Z1 has been set equal to the exact nominal distance between target surface and video camera in the above equations, solving for $z_i$ will yield a value at the apex of the target surface which is equal to the deviation of Z1 from nominal. This measured deviation in Z1 is not affected by additional displacements of the target surface in either the X or Y axes—the value of these displacements can readily be determined by measuring the distance between the zero values of x and y and the values of x and y at the $z_i$ apex. These properties provide a means for implementing a feedback control system whereby the video camera can maintain optimum focus and centering of the projected grid pattern.

The foregoing equation set is henceforth referred to as the topography algorithm.

A preferred embodiment for achieving the goals of the invention begins with the selection of the human cornea as the target surface to be measured. The projection system 1 of FIG. 1 is powered by a pulsed laser having a wavelength of 523 nm whose output is expanded through a diverging beam to project a grid pattern of approximately 8 mm diameter on the cornea. This 8 mm diameter is chosen because it is representative of the normally useful optical diameter of the human cornea. The axis of the beam is selected to have a 22.5 degree angle with respect to the optical axis of the video camera 7 on the horizontal or X-Z plane. With this 22.5° angle, a one unit difference in elevation on the cornea translates to about a 0.4 unit difference as viewed by the video camera 7. In the vertical or Y-Z plane, the angle with respect to the optical axis of the video camera 7, as stated previously, is zero.

Figure 4:
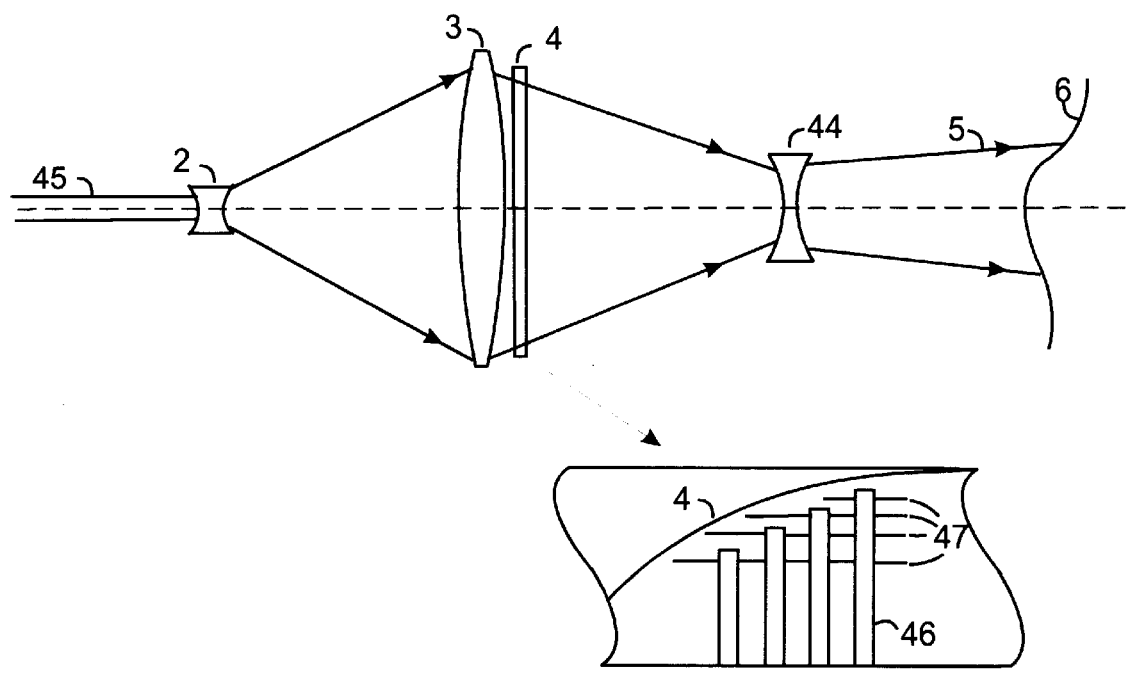
FIG. 4 shows the elements of the collimated ray grid projection system of the preferred embodiment.

FIG. 4 shows the elements comprising the projection system 1 of the preferred embodiment: The 1 mm diameter beam 45 of the laser is expanded by a concave lens 2 to a cross section of 80 mm whereupon a converging lens 3 directs the beam through a mask 4 consisting of 0.75 mm vertical apertures or slits (e.g., a Ronchi grating) separated 0.2 mm from each other. At a distance of about 40 mm from the mask 4 a concave lens 44 diverges the projection rays 5 to result in about an 8 mm cross sectional diameter grid pattern on the cornea; the focal point from which the grid pattern rays emerge is at a distance required to insure the topography measurements are independent in the corneal distance from the video camera, as previously discussed and illustrated in FIG. 3. Because the nominal distance Z1 between the cornea and lens 9 is 400 mm and the angle of incidence of the central projection ray is 22.5°, the projection ray focal point measured along the projection system axis 35 is 400/cos (22.5°)=432.96 mm from the cornea. By means of this cornea position independent projection system technique and the fact that the axis of the projection system and the optical axis of the video camera are coincident in the Y-Z plane, the vertical position of the elements of the grid pattern imaged on the CCD is invariant: For example, movement of the cornea in any direction (X, Y, or Z) does not affect the vertical positions of intensity points imaged on the CCD. The reason for this particular implementation of the projection system 1 is to achieve a means for limiting diffraction spreading to an acceptable level: If the mask was 8 mm in diameter rather than the selected value of 80 mm, and the vertical openings 0.075 versus 0.75, then at a distance of 25 mm from the cornea (a practical minimum value to avoid interfering with ablation apparatuses and permitting full view by the video camera 7), then the horizontal distance from maximum intensity to the first intensity zero on the cornea would be about 0.22 mm—a value that would limit maximum intensity to minimum intensity variations to about only 2 to 1 for the 0.2 mm slit spacing. Such a broad peak intensity profile would degrade the accuracy with which the fractional pixel position could be determined and, at least for this reason, the present implementation of the projection system offers one possible means for ameliorating the diffraction problem: The 0.75 mm vertical slits of the 80 mm mask result in a diffraction spreading only one tenth that of the 0.075 mm slots in the 8 mm mask for a given mask distance. Therefore, the short focal length converging lens allows the distance between the mask and cornea to be about 65 mm for which the first intensity zero on the cornea from the peak would be about 0.08 mm. By selecting the width of the slit openings in mask 4 to be 0.75 mm, the overall projected width of the bright vertical lines on the cornea is minimized when diffraction is taken into account.

The selection of vertical slits for the mask apertures rather than circular holes has an advantage in that the diffraction widening of a narrow rectangle of collimated light is about 20% less compared to a circular hole having the same diameter as the slit width. A greater advantage relates to the potential for both improving accuracy of measurement and compensating for undetected grid points. In utilizing such desirable benefits, it is first noted that whether the peak detection procedure is conducted on all of the rows of pixels or only those rows needed to provide the desired 0.2 mm square grid measurement pattern, there is no difference in the time required to complete the collection of MCC values.

Because there are about 25 pixels vertically between the desired L grid points, then by processing every row, even if some intensity peaks in the desired selected rows are missing, those peaks in adjacent rows can be used to interpolate the missing MCC value. Optional approaches include: Measuring several adjacent rows on either side of the selected row and always averaging with the selected row; spatially filtering each of the series of x positions corresponding to a vertical slit; averaging only if the selected row data is discarded due to a failure to detect valid intensity peaks.

The failure to detect valid intensity peaks presents the following problem: As the MMC values corresponding to CCD coordinates are detected they are consecutively entered into memory in matrix form, so the first missing peak value along a row of pixels mean that all successive peaks in that row will be associated with incorrect projection rays. Possible means for averting this problem are discussed as follows: Because of the circular confines of the cornea, limiting the projected grid pattern to a circular boundary of 8 mm diameter will permit imaging of the entire grid pattern. In FIG. 4, an expanded view of a section of the mask 4 shows a more or less circular boundary for the vertical slits thereby constraining the grid pattern to be similarly circular. Now, by choosing the lengths of the mask slits so that on selected rows of pixels separated by 0.2 mm, the number of intensity peaks that should be present is unambigiously determined for the selected rows of pixels. Therefore, by counting the number of peaks along selected rows and comparing with the required number, any occurrence of missing points in a given selected row can be detected. This resulting information can be used either to discard the row data and move onto the next selected row, or in a more complex approach, to back check the row to find the approximate position of the missing peak(s) and then, from the intensity peak positions of two or more of the preceding adjacent row(s), find peak positions sufficiently close to the approximate positions of missing peaks in the present selected row and extrapolate these to produce the positions of the missing peaks in the present selected row—if this cannot be done, then all the row data of the present selected row is discarded.

The method of designing the required aspherical surface on converging lens 3 is defined in U.S. Pat. No. 5,490,849: For the present invention, the method begins with back projecting the meridional rays of the desired projection rays 5 through the diverging concave spherical lens 44, through the mask 4, and through the rear spherical surface of the converging lens 3; next, rays from the diverging lens 2 are intersected with the back projected rays and then by an iterative procedure the slope of the aspheric front surface of converging lens 3 is determined.

The video camera 7 consists of a polarizing filter 8, a 20 mm diameter biconvex objective lens 9 having an aspheric front surface, an 8 mm concave-plano field-flattening lens 10 in close proximity with the CCD, and the CCD 11 itself. Because the projection light source selected is a laser, there is no need to consider chromatic aberration in the design of the optical system. The distance between the objective lens and the target surface/cornea is 400 mm. This relatively large distance is chosen for several reasons: 1) the greater the distance, the smaller the number of specular reflected rays reaching the optical system, desirable because, although the polarizing filter greatly attenuates such rays, it cannot eliminate them completely; 2) the need to provide sufficient depth-of-field allowing adequate focussing of the grid points across the surface of the cornea; 3) the desire to avoid having a too rapidly diverging projection system beam, the divergence being selected to minimize the effect of differences in distance between the cornea and the video camera objective lens on the measurement accuracy; 4) provide ample room for the laser ablation apparatus.

The following is an example design for the video camera optics that enables imaging all of the points of the 8 mm span of the projected pattern to within a blur diameter of 0.03 mm on the CCD, and doing so over a range of corneal curvatures ranging from 6.8 m to 9.5 mm: The objective lens 9 has a refractive index of 1.5, a front convex hyperboloidal surface defined by a Schwarchild constant SC=−4.5 or an eccentricity e of 2.12, and having a paraxial radius of curvature of 200 mm, followed by a spherical convex back surface of radius 200 mm 2 mm distant; the field-flattening lens 10 has a refractive index of 1.91 and is at a distance of 397 mm from the objective lens; it has a concave hyperboloidal surface defined by an SC=−2.43 or e=1.56, a paraxial radius of curvature of 3 mm, a central thickness of 1.8 mm and a flat rear surface. A further result of these design parameters is that distortion of the grid pattern is limited to about 0.003 mm. Although these design values are not necessarily optimum, they do demonstrate that the single element aspheric objective and aspheric field flattening lenses can achieve the necessary depth of field, uniformity of focussing and linearity over a broad range of human corneal shapes.

Figure 5A:
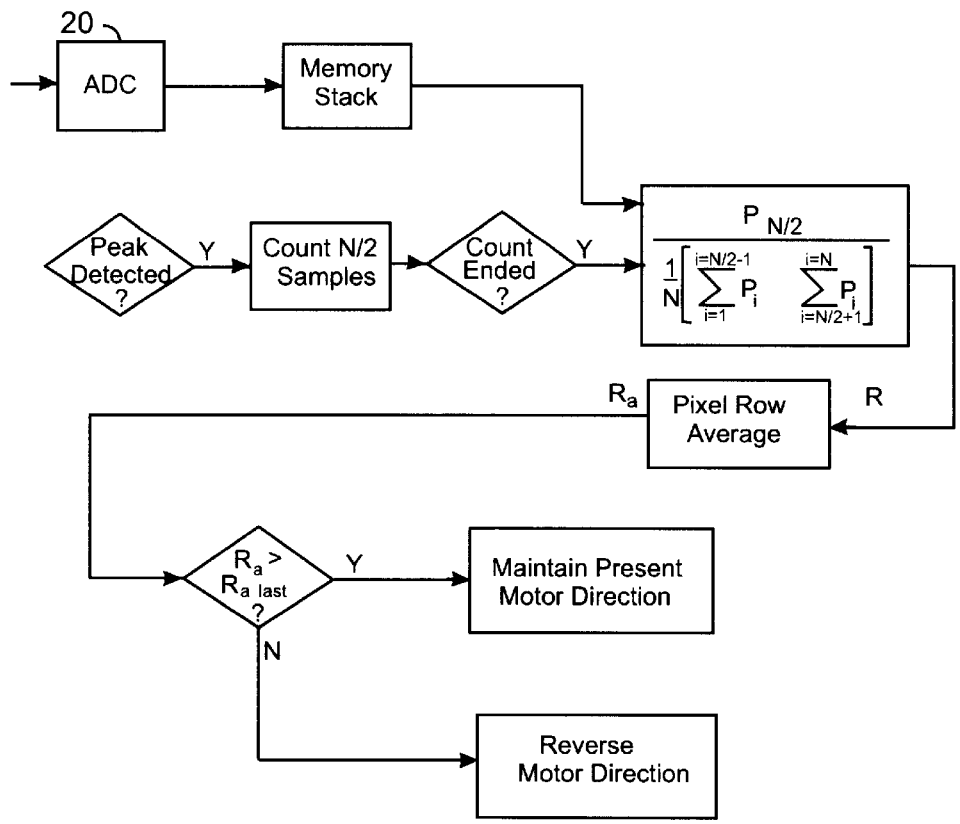
FIG. 5a is a flow diagram of the method of iterative automatic focussing for the present invention; 5b is a direct servomechanism focussing controller in three dimensions.

Because the depth of field of the preferred embodiment video camera design is only about 1 mm, it is desirable to provide an automatic focussing means so that movements of the in-vivo cornea do not degrade the necessary sharpness of the grid pattern image. This automatic focussing system is not designed to compensate for saccadic eye movement, but is used only for initial acquisition of the grid pattern image on the cornea and the maintenance of focussing as slower movements of the cornea occur over the duration of a typical PRK surgical procedure. The elements of the focussing system include: A means for moving the projection system and the video camera on a common frame of reference or platform using widely available servo-mechanism means, a feedback signal derived by processing the output of the CCD in such a way as to maximize the sharpness of the voltage peaks and hence the sharpness of the grid pattern image points. Many techniques are available for implementing this peak maximizing; however, care must be taken because the intensity peak amplitudes may have considerable variation over the corneal surface and the most rapid change in intensity from pixel to pixel on the CCD does not necessarily correlate to the narrowest peak, i.e. minimum blur diameter. Therefore, the technique selected for the preferred embodiment uses the ADC 20 of FIG. 1 in conjunction with a temporary memory block which stores the last five digitally converted CCD output values then, two converted values after a peak is detected, the ratio of the peak to the averaged values on either side of the peak is taken as a measure of the sharpness of focus. An average over each pixel row readout is made of these ratios and this averaged value is attempted to be minimized by the movement of the platform in the direction of the cornea. The flow diagram in FIG. 5a shows the elements of this iterative type of control algorithm using an arbitrary number N rather than 5 converted output values.

Figure 5B:
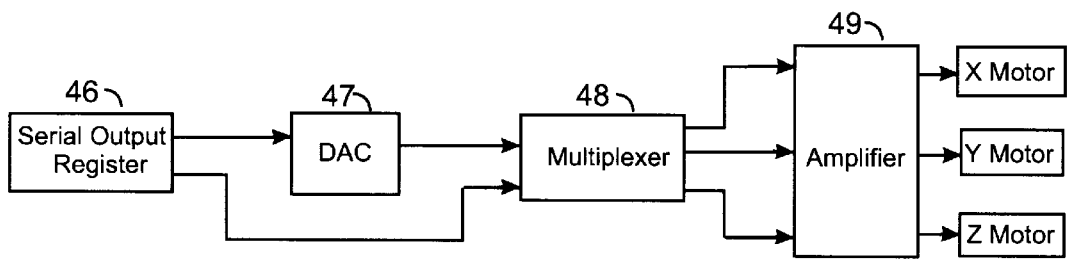

As mentioned above in the discussion of the topography algorithm, once the elevation points for a single CCD frame have been calculated, any variation from the nominal cornea/target surface to video camera separation (Zl) can be found by checking the value of $z_i$ at the apex of the cornea. If this separation is the nominal value Zl, $z_i$ at the apex will be zero; if the separation is less than Zl, $z_i$ at the apex will be a negative value equal to the actual separation—a separation greater than Z1 gives a positive value equal to the actual separation. This characteristic of yielding an error value either side of zero is optimum for implementing a linear, sampled-data servomechanism: For example, if the CCD frame readout is 20 per second thereby yielding 20 error samples per second, a non-overshooting response time of less than half a second can easily be obtained for adjusting the platform in the Z direction; and, because similar error signals can be derived for corneal displacements in the X-Y plane—which is normal to the Z-axis. Therefore, a three-axis platform controller can be implemented as shown in FIG. 5b. A digital to analog converter (DAC) 47 converts a vector of values out of a serial register 46, where these values comprise: deviation from Z1, deviation of the corneal apex position from the X-axis origin, and deviation of the corneal apex from the Y-axis origin; then a multiplexer 48 routes each successive analog error value to a three channel motor drive amplifier 49, the outputs of which drive the respective platform motors to minimize the errors in the three axes.

Other elements of the preferred embodiment requiring special design consideration are the CCD 11 and the laser light source of the projection system 1. Because the in-vivo eye displays a range of jerky movements—saccadic eye movement—it is necessary to capture the projected grid image quickly to avoid smearing of the image and hence degrading the topographic measurement. In some PRK procedures a Thornton vacuum ring is used to immobilize the eye thereby greatly reducing the amplitude of saccadic movement and concomitantly the grid image capture speed requirement. To widen the application of the preferred embodiment to encompass worst case conditions of saccadic movements, a pulsed laser having pulse widths around 10 ns will freeze the projected grid image so that even rapid saccadic eye movements will have negligible effect on the measurement accuracy. Although the peak power output of the selected laser is some 4000 watts, the 10 ns pulse width is brief enough to result in an average intensity of the grid pattern of only some 50 lux (lumens per square meter). Normal operating room environments are around 500 lux, so the video camera must utilize a high speed shutter synchronized with the pulsed laser output so as to capture as much of the laser produced image as possible to the exclusion of ambient light sources. Present day electronic shutters are capable of operating at 10 us, so that the ratio of average laser illumination to ambient illumination of 0.1 (=50/500) can be increased to 10000 to one thereby making the ambient light interference negligible. If a lower laser power and/or a laser with low peak power, long duration pulse widths is employed, a bandpass filter tuned to the laser wavelength may be used to achieve the required ambient light rejection.

Figure 6A:
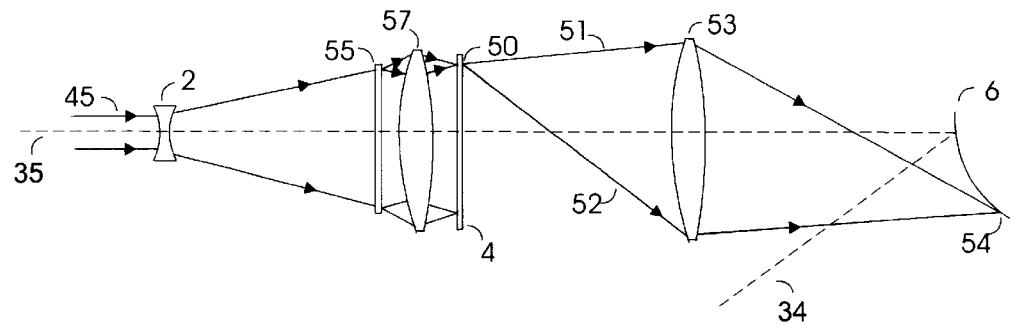
FIG. 6a shows an alternate embodiment of the invention for the elements of a projection system using conventional optical means; 6b shows the substitution of optical fibers for the conventional optical means.

FIG. 6a presents an alternate means for implementing the projection system 1 which differs from the strategy of FIG. 4 in that it does not utilize substantially collimated rays to project the grid pattern; rather, it uses the principle of the classic projector as shown by the rays drawn from points on the mask 4. Here, for the projection principle to function properly, the light intensity emanating from an arbitrary mask point 50 and impinging on the projection lens 53 must be relatively constant over the span of rays encompassed by rays 51 and 52. Because of the collimated nature of the laser radiation, the use of the negative/concave lens 2 to diverge the beam is not usually sufficient by itself to obtain this level of dispersion or diffusion. A diffuser 55, such as a ground glass plate, onto which the diverged laser beam is directed can yield the required dispersion by selecting a granularity of the plate only large enough to produce the needed dispersion in order to maintain reasonable light efficiency. Converging lens 57 functions to further improve light efficiency. At the focus point 54, the sharpness of focus is diffraction limited by: $d=2.44L\lambda/D$ where L is the length from lens to mask, $\lambda$ is the laser wavelength, D is the lens 53 diameter and d is the minimum blur image diameter due to diffraction. As observed in this formula, the size or shape (circular holes or slits) of the mask apertures have no effect on the blurring due to diffraction—only the focal ratio of the projection lens 53 is a factor along with wavelength. Therefore, the mask apertures can be made as small as desired. However, the total blur dimension has a minimum value equal to the sum of blur due to the projecting lens 53 aberration and diffraction limit. As previously discussed, to make the topography measurement independent of corneal distance variations then it is required that the distance from the center of lens 53 and cornea be 400 mm, and the distance between the cornea and the focal point of the projection system along the Z axis also be 400 mm. With the further specification that the axial corneal distance variation may depart from nominal (Z1) by +/−0.5 mm to restrict the blur diameter from exceeding 0.03 mm (not including diffraction), the diameter of lens 53 becomes 13 mm for which the diffraction blur is 0.042 mm yielding an overall minimum blur diameter of 0.072—for imaging an infinitesimal point—or equivalently a distance from an intensity peak to a zero of 0.036 mm. By specifying a mask aperture width of 0.025 mm the distance between an intensity peak and intensity minimum (zero) is about 0.05 mm. Use of the same design for projection lens 53 as for objective lens 9 of the video camera results in a near optimal focussing property.

Figure 6B:
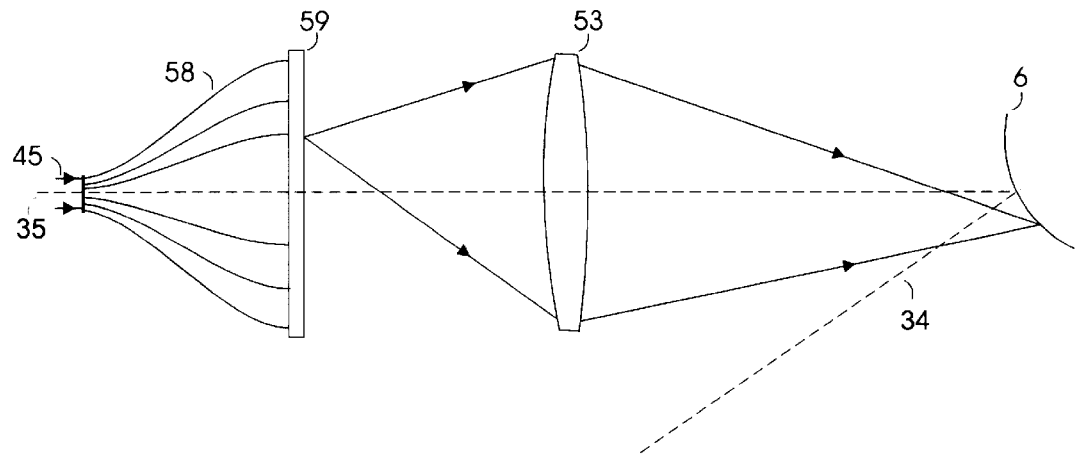

A disadvantage of FIG. 6a is that even with an optimum diffuser 55, the use of 0.025 mm wide vertical slits with 0.2 mm spacing gives a light efficiency of at best of 12%. By the use of optical fibers 58 shown in FIG. 6b, about 80% of the laser output can be imaged on the cornea. This is done by bundling the input end of the fibers tightly together to allow them to collect almost all of the 1.0 mm diameter laser beam radiation 45. The fibers are then inserted into holes in the alignment mask 59 in such a way that the axes of the optical fibers all converge on the approximate center of the projection lens 53. A disadvantage of this fiber optic implementation involves primarily the difficulty in fabricating the alignment mask 59.

Some further considerations involved in the design of the preferred embodiment are as follows: Because of considerable variation in the diffusiveness of an ablating corneal surface, and the speckle effect of the laser radiation (an effect than can be minimized using a noncoherent laser), a fairly wide range can be expected in peak image intensities. Setting the threshold of peak detection at an amplitude of about one-fifth the maximum peak intensity should be sufficient to insure detecting all of the grid points. In order to determine the true position of the intensity peaks imaged on the CCD it is necessary to select a type of CCD that insures that virtually all the impinging photons are detected; otherwise a peak in intensity could fall between pixels where it would be undetected and could lead to inaccurate determination of the position of the intensity peaks. The so called back illuminated CCD design provides a means for avoiding this problem which is of concern primarily on the analog level because of time differentiation performed on the CCD output. In comparison, the analog-to-digital CCD output voltage converter (ADC) 20 does not need to have a particularly high accuracy so long as it can resolve reasonably significant amplitude differences occurring between adjacent pixels. Using 8 bits for the ADC 20 provides a balance between insuring adequate intensity amplitude resolution and maximizing conversion speed. The master clock counter MCC 15 outputs a binary value which is reset at the end of the readout of the last row of the CCD. Since in this preferred embodiment there are 1048576 (1024×1024) total CCD pixels and there are 16 master clock counts for each pixel readout, the counter register must have 24 bits. Therefore, the counter value and the 8 bit amplitude value may be combined into one 32 bit data word and thus, in addition to being compatible with PC computers, will speed the data input into the computer.

Figure 7:
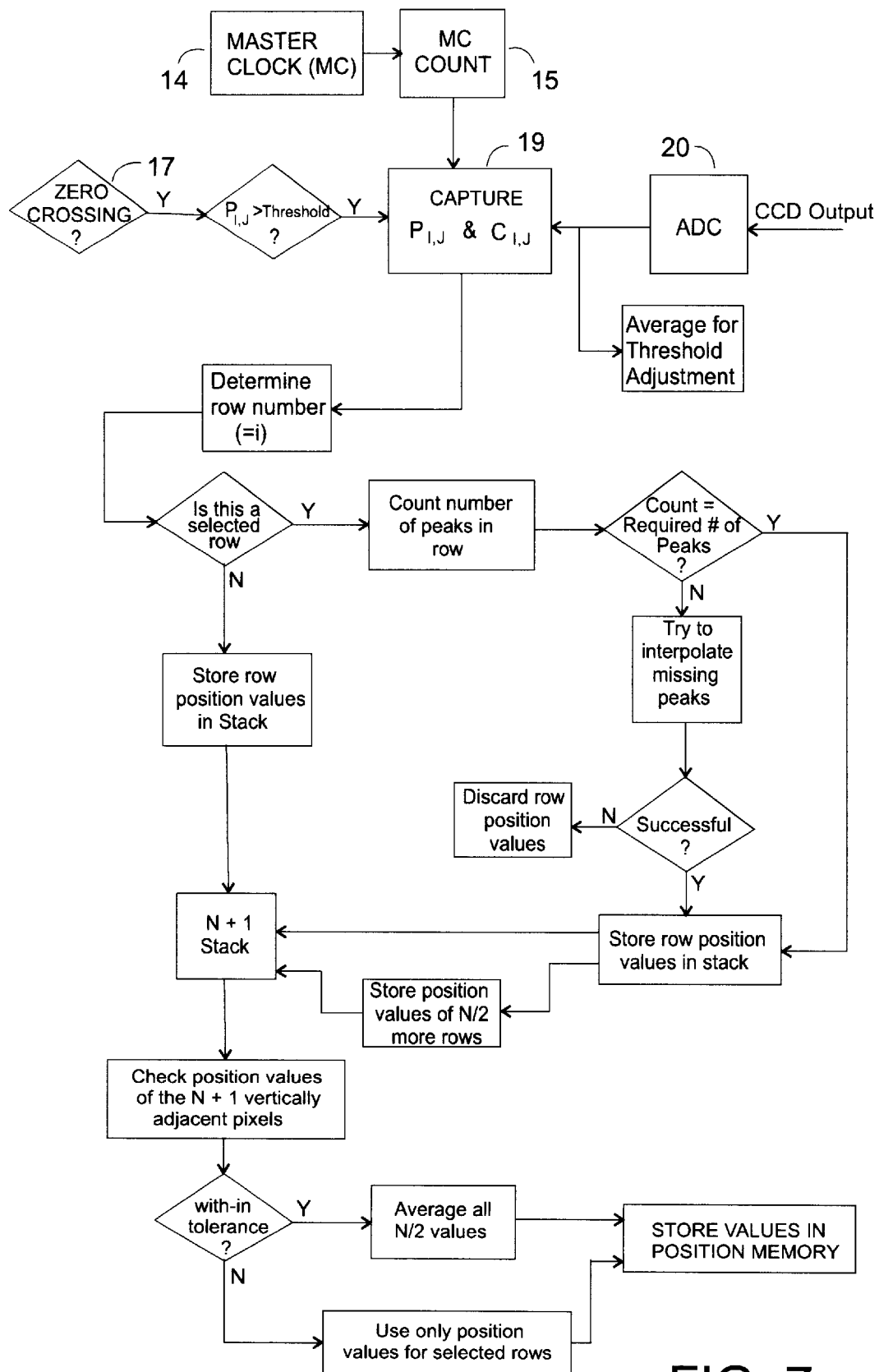
FIG. 7 is an overall flow diagram of the method of the present invention.

FIG. 7 is the flow diagram applicable to the preferred embodiment of the invention. As seen, it recapitulates the block functions of FIG. 1 and shows in addition the processes of intensity threshold adjustment together with the above referred to procedure of averaging the detected position (MCC count) several rows (N/2) on either side of the selected row.

To adjust the threshold intensity level, an average intensity of all the peaks is calculated for each CCD frame. At the end of the CCD readout, one fifth of this average intensity is used as the threshold setting below which any intensity peak will be discarded. The factor of one fifth can be adjusted either higher or lower depending on whether the number of detected peaks is greater or fewer than the actual number of peaks, respectively.

Figure 8:
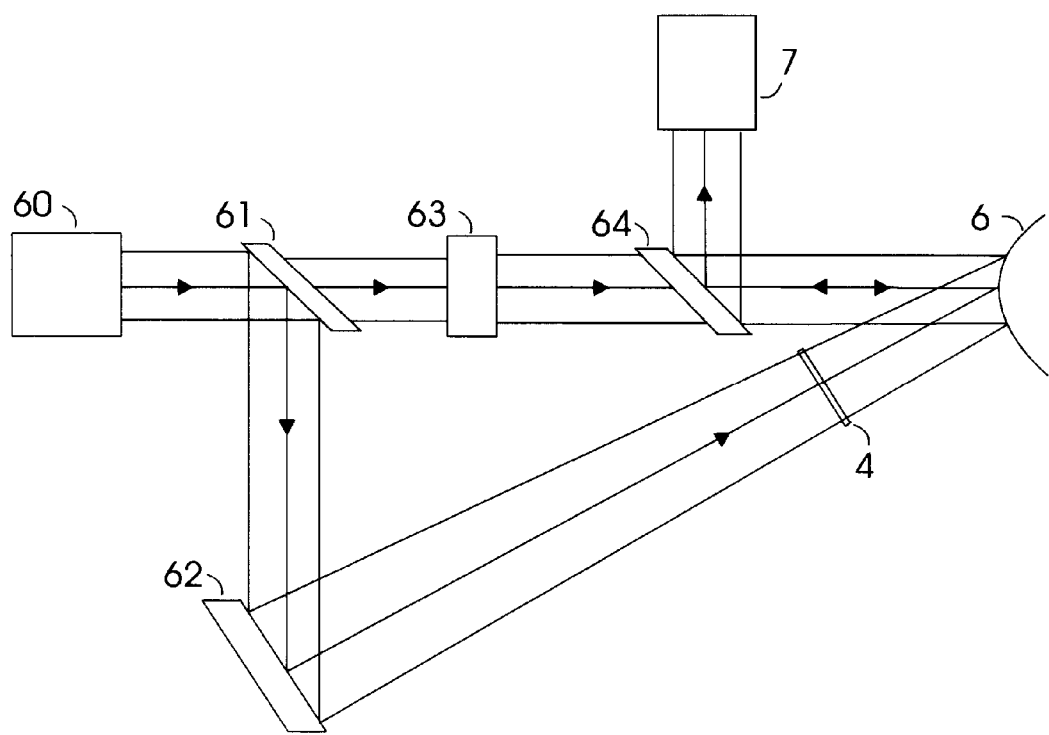
FIG. 8 shows an alternate embodiment incorporating an ultraviolet source of radiation for the grid projection system.

An alternate embodiment, diagrammed in FIG. 8 displaces the existing projection light source with the ultraviolet light from the photoablation device which will be in a range of 150 to 200 nm such as a 193 nm excimer laser whose collimated beam 60 already has the required cross section for projecting the grid pattern on the cornea. Mirror 61 transmits about 90% of beam 60, the remainder being reflected to a second completely reflecting mirror 62. The resulting collimated beam from mirror 62 is passed through the mask 4 which forms the grid pattern projected on the cornea 6. The laser beam modulator 63 is controlled, using feedback from the means of this invention, both to modulate the beam through the mirror 61 for purposes of corneal ablation and to completely attenuate the beam on alternate laser pulses during which periods the projection grid points are imaged by the video camera 7 which is comprised of 193 nm transmissive optical components. The semireflecting mirror 64 performs the function of allowing the video camera to lie on the same axis as the ablating beam; depending on the laser ablating technique, this mirror may or may not be needed; it transmits about 90% of the modulated high power laser beam to the cornea, and reflects the diffuse radiation from the projected grid image on the cornea towards the video camera 7. An advantage of such a system is a significant reduction of diffraction effects enabling higher resolution of the imaged grid points by reducing diffraction spreading by about a factor of 3. Another possible benefit to the use of the ultraviolet radiation for imaging is that the ablating corneal surface may result in more diffuse and less specular reflection.

In a variation of this embodiment, the presence of fluorescing substances contained in or applied to the target object—such as potassium salts—can be utilized to create the desired grid projection image in visible light. In such an implementation, the video camera does not require ultraviolet transmissive optics or a CCD sensitive in the ultraviolet radiation and the modulator 63 does not have to block radiation on alternate pulses.

An adjunct embodiment of the application to corneal topography in the course of corneal photoablation is the use of an additional 2 dimensional photodetector sensitive only in the 8 um infrared light region known as a quantum well infrared photodetector (QWIP). The motivation for this device derives from the fact that excimer laser corneal ablation is accompanied by an increase in temperature of the ablated surface. Therefore there is a need to be able to monitor the corneal surface to guard against regions of overtemperature (hot spots) and also to provide a feedback to the photoablation source to refrain from ablating of such overtemperature regions until the temperature is within acceptable limits. A typical QWIP is about the same overall size of the CCD of the preferred embodiment and comprises a square 256×256 array of pixels thereby enabling a finely detailed temperature profile of the cornea.

Figure 9:
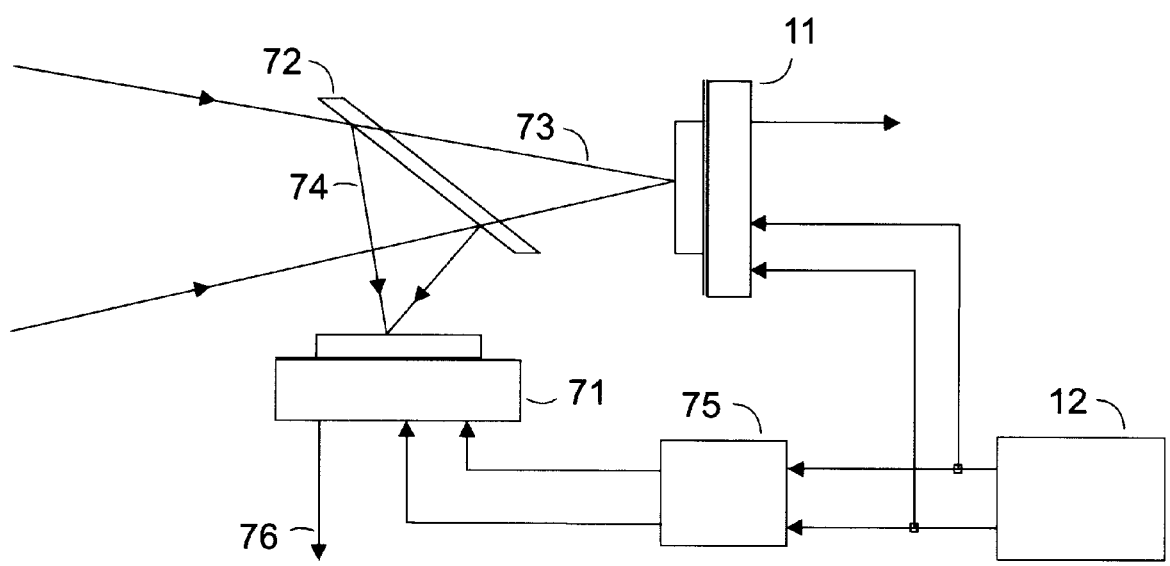
FIG. 9 shows an adjunct means for performing two dimensional temperature profiling concurrent with the present invention.

FIG. 9 gives one implementation of this alternate embodiment which provides a combination of elevation and temperature topography. A heat reflecting mirror 72, reflects most of the infrared light 74 to the QWIP 71, while transmitting most of the laser light 73 used in the topography process to CCD 11. The QWIP pixel readout is synchronized to the readout of the CCD by a frequency dividing means 75. Because the QWIP selected has 256×256 pixels compared to 1024×1024 pixels for the CCD 11, the dividing factor is 4, and in addition, a pause is inserted equal to 4 CCD rows before progressing to the next QWIP row. This enables the QWIP output 76 to be associated with the regions of the cornea defined by the grid image. In FIG. 9 it is assumed that a common optical system is used for both wavelengths which would require an objective lens material to be transmissive over a range of about 0.5 um to 8 um; materials such as zinc sulfide have this property. Alternatively, a separate optical system comprising an 8 um transmissive objective and QWIP can be implemented.

As successive CCD frame data, in the form of grid pattern row-column intensity peak positions, are computed to produce the surface topography in three dimensional space, many presentational means are available for display. For example, real time display software such as MPEG-1 and MPEG-2 can provide a flicker-free video graphical display of the differential topography in wireframe, Gouroud shading 3D format. Also, digital filtering algorithms can be used to insure that the graphical display is jitter free with negligible error relative to the actual topography of the target surface. In addition to graphical display, these same filtering techniques can be used to provide the topographical feedback for automatic photoablation control of PRK and PTK.

In addition to corneal topography, the invention contemplates application to assembly lines where manufactured articles having semi-diffuse surfaces could be topographically measured to within a few microns at rates approaching several dozen articles per second. A triggering means activates the pulsed laser and video camera shutter when each article is properly positioned. For articles having a smooth (specular) surface, such articles could first be cooled to cause moisture to deposit on their surfaces in the form of a microscopic fog that would create the required diffuse surface for topographic measurement.

Within the spirit of the invention no constraint is intended to be placed on the following: Wavelength, pulse duration, polarization, whether radiation is coherent or incoherent, or power output of the monochromatic projection light source (laser); the number and type of elements (lenses or mirrors) in the optical system used for the video camera; the number of pixels, the frames captured per second, sensitivity, electronic shutter speed, method of readout (row by row or random), or technology of manufacture of the CCD; the pattern or shape of the holes or apertures as to the manner in which light is conducted to the holes or apertures (e.g. optical fibers) of the mask. Also, no constraint is contemplated on how the hardware function of the invention is implemented; for example, memory storage requirements may be satisfied using direct memory access on a high speed desk top computer together with the computational algorithms; or, all functions can be incorporated in a customized application specific integrated circuit package with only the final topography coordinates going to a computer for display and feedback control of the photo ablative delivery system.

I claim:

1. A system for rapidly measuring the topography of a semidiffuse target surface comprising:

a projection source means comprising a laser producing a pulsed plane polarized light beam having a substantially uniform intensity cross section, said light beam passing through a mask, said mask having apertures to form a grid pattern, said light beam through said grid pattern projecting sharply defined bright and dark areas on the semi-diffuse target surface;

a video camera means comprising a polarizing filter, image forming optics and a CCD (charge coupled device), said camera forming on the CCD an image of the grid pattern projected on said target surface, the polarizing filter blocking specular reflected light and passing diffuse reflected light from said image on the target surface;

a focussing means whereby said projection source and the video camera are mounted on a common platform, said platform being movable as to maintain focus and positioning of the grid pattern on the CCD;

a master clock producing low jitter constant frequency pulses;

a frequency divider receiving pulses from said master clock and delivering pulses at a reduced repetition rate to the CCD so that a single pixel readout occurs for each of the reduced repetition rate pulses, said readout resulting in an output voltage from the CCD proportional to pixel light intensity;

a master clock counter giving a count of all pulses from said master clock over a time period corresponding to a complete readout of the pixels of the CCD, said count precisely identifying the pixel location on the CCD;

an analog circuit assembly consisting of a differentiator, zero crossing detector, and gate circuit, said assembly enabling the capture of the master clock count at an instant when a voltage peak corresponding to a light intensity peak is outputted by the CCD and when said voltage peak is above a threshold value;

a digital register, into said register is stored the master clock count at the instant an enabling pulse is issued by said gate circuit;

an analog to digital converter producing a digital equivalent of the CCD output voltage, said digital equivalent being stored in said digital register simultaneous with storage of said master clock count, said converter being used to provide a feedback signal to automatically control movement of said platform;

a digital computing means, either in an application specific integrated circuit (ASIC) or computer based, performing in real time the functions of temporary storage, averaging, interpolation, error correction, topography calculation and displays.

2. The system of claim 1 where the CCD is a high efficiency back illuminated type with electronic shuttering on the order of microseconds.

3. The system of claim 1 where said laser produces pulse widths on the order of nanoseconds, and where pulsing is synchronized with the electronic shutter on the CCD.

4. The system of claim 1 where said source projection means comprises:

a concave lens to expand the beam of the laser producing a diverging beam;

an aspherical front surface convex lens with a spherical rear surface, said lens having a diameter greater than the diameter of the desired projected grid pattern, said convex lens capturing said diverging beam when said diverging beam has expanded to the diameter of the convex lens, said convex lens rapidly converging said diverging to form a rapidly converging beam;

a mask placed in close proximity to the rear surface of said convex lens, said mask apertured to form a pattern of vertical slits said pattern of vertical slits having a circular boundary producing a cross sectionally modulated converging beam;

a second concave lens placed at a distance from said mask capturing all of said modulated converging beam at a desired diameter, said second concave lens producing a slightly diverging beam, the cross section of said slightly diverging beam preserving the pattern of vertical slits sufficiently free from diffraction blurring at a maximized distance from the second concave lens.

5. The system of claim 1 where the source projection means comprises:

a concave lens to expand the beam of the laser producing a diverging beam;

a diffuser receiving said diverging beam, said diffuser producing disperse light beam;

a convex condensing lens capturing said disperse light beam, said condensing lens directing the disperse light beam through said mask;

an aspherical projection lens imaging the disperse light through said mask on said CCD.

6. The system according to claim 5 where the concave lens, the condensing lens, and the diffuser are replaced by a bundle of optical fibers, said fibers being bundled closely together at one end so that the normally narrow beam of the laser spans the bundle of fibers, each of the opposite ends of said fibers being separated and inserted into an alignment mask, said mask constraining said fibers to form a grid pattern directing each fiber towards said projection lens.

7. The system according to claim 1 where said semidiffuse target surface is a deepithelized human cornea, said cornea reflecting diffuse light from said projected grid pattern, said cornea undergoing photoablation.

8. The system according to claim 1 where said image forming optics comprise an objective lens nominally placed 400 mm from said target surface, said objective lens being separated from the CCD by nominally 400 mm, said objective lens being biconvex with equal paracentral radii of 200 mm with a spherical rear surface and an aspherical front surface, the front surface being hyperbolic with an eccentricity of 2.12, said objective lens being 2 mm thick, 20 mm in diameter and having an index of refraction of 1.5;

a field flattening lens having a concave front surface with a paraxial radius of curvature of 3 mm and an eccentricity of 1.56, said field flattening lens having a central thickness of 1.8 mm and a flat rear surface, said field flattening lens having an index of refraction of 1.91.

9. The system of claim 1 where said focussing means comprises a digital to analog converter (DAC), said DAC receiving from said digital computing means values of errors from nominal positioning of said target surface along a set of three dimensional axes, said DAC outputting to a multiplexer a sampled set of three voltages proportional to said errors from nominal portioning, said multiplexer routing said sampled voltages to three motors, said motors driving said platform along said axes in directions to minimize said errors.

10. The system of claim 1 where said laser light source produces pulsed ultraviolet radiation of 150 to 200 nanometer wavelength, said laser being an excimer laser, said excimer laser being used to perform photoablation on a cornea, said excimer laser producing a beam of crosssectional diameter about equal to a desired projection diameter along an axis onto said cornea, said beam being diverted by a partially reflecting mirror to a second mirror to form an intensity attenuated beam, said second mirror displaced from said axis and reflecting said attenuated beam through said mask forming the grid pattern on the cornea, said laser beam being blocked by a modulator on alternate laser pulses, during said alternate pulses the grid pattern on the cornea is imaged by said video camera onto a CCD sensitive to said ultraviolet radiation wavelength.

11. In claim 10 the system where said video camera images a fluoresced projected grid pattern, said fluoresced pattern being caused by fluorescent material contained in or applied to said cornea.

12. The system of claim 1 where said video camera comprises:
   an objective lens transparent to both laser and infrared radiation, said infrared radiation being of wavelength in the 8 nanometer range;
   a mirror reflecting said infrared radiation but transmitting said laser beam;
   a quantum well infrared photodetector (QWIP) receiving said infrared radiation, pixel readout of said QWIP being synchronized with the CCD readout, said infrared radiation emanating from the surface of a cornea undergoing photoablation, said QWIP being sensitive to a range of infrared radiation variations resulting from temperature increases induced in the cornea by said photoablation.

13. A method for performing high speed topography measurements of a semi diffuse target surface comprising the steps of;
   aligning a light source to project through an apertured mask a cross sectionally modulated grid pattern;
   projecting said grid pattern on said target surface;
   imaging, using an objective lens, said grid pattern on a CCD with sufficient resolution to achieve a desired topography accuracy;
   setting a pulse repetition rate of a master clock at a rate higher than the rate at which light intensity at successive pixels is measured;
   reading out a voltage from the CCD proportional to light intensity of each pixel of the CCD, the step of pixel readout being performed at a submultiple of the pulse rate of the master clock, the step of pixel readout producing an output voltage as a function of time;
   counting the pulses from the master clock to produce a count during the readout of the pixels of the CCD, resetting said count to zero upon completion of the readout of all of the pixels of the CCD;
   capturing said counts precisely when peaks are detected in said output voltage, said peaks corresponding to peaks of light intensity;
   storing said captured counts in memory, correlating the counts with two dimensional coordinates on the CCD corresponding to said detected peaks;
   calculating three dimensional coordinate points corresponding to the topography of the target surface from said two dimensional coordinates.

14. The method of claim 13 where the step of aligning a light source also includes the steps of:
   defining a projection axis from said light source through said target surface, defining an optical axis between said surface and said imaging means, defining a horizontal plane;
   aligning the projection axis and the optical axis to both lie in said horizontal plane, aligning the projection axis and the optical axis to intersect on the target surface at a non-zero angle on said horizontal plane;
   locating a focal point along said projection axis at a point corresponding to the center of said objective lens as measured relative to said optical axis, diverging light rays from said focal point through said mask resulting in an expanding grid pattern, projecting this pattern onto the target surface.

15. The method of claim 13 where the step of imaging includes the steps of:
   converting to digital form the successive pixel intensity values readout from the CCD;
   storing N most recent values of said successive pixel intensity values and after detecting a peak intensity value, storing N/2 more successive pixel values before;
   forming a ratio of said peak intensity value to an average of remaining N—1 intensity values;
   iterating the step of forming a ratio to produce a sequence of ratios;
   forming an average of said ratios across a full row of pixels to produce a present row average;
   checking said present row average with a previous row average, checking direction of motion of a focussing means;
   modifying said direction of motion to increase said present row average depending on whether said previous row average is greater or less than the present row average.

16. The method of claim 13 where the steps of reading out pixel intensity, counting master clock pulses, and capturing the master clock count also involve the step of reading out all pixel rows of the CCD in the presence of a vertical slot grid pattern image with a circular boundary followed by the steps of:
   selecting those rows of the CCD to produce the same approximate spacing as that of the vertical line image spacing resulting in selected rows;
   adjusting the length of said vertical slots so that the number of light intensity peaks occurring across each selected row is a predefined number;
   temporarily storing the count captured at intensity peaks over several consecutive rows of pixels;
   checking the number of light intensity peaks actually detected in a given selected row and if fewer than said predefined number, back checking the positions in said given selected row to determine approximate positions of missing peaks, then
   comparing peak positions in several previous adjacent rows with said approximate positions and if sufficiently close, extrapolating these previous positions to produce extrapolated peak position values, otherwise discarding all position values in this row containing missing peaks;

averaging the counts for each vertical line one or more rows on either side of each said selected row.

17. The method of claim 13 where the step of reading out a voltage is followed by the steps of:

differentiating with respect to time the voltage out of the CCD by means of a differentiator;

detecting a transition from a positive to a negative voltage out of the differentiator and triggering a gate circuit to produce a sharp voltage pulse if the voltage out of the CCD is above a threshold value, if so sending said pulse to cause capture of the master clock count value.

18. The method of claim 13 where the step of capturing said count includes the steps of:

dividing master clock pulse frequency by a factor producing a pulse interval, said interval corresponding to the interval between successive pixel readouts of said CCD;

setting said factor so that the number of master clock pulses between successive pixel readouts corresponds to the desired positional resolution of light intensity peaks on the CCD;

adjusting the master clock pulse frequency to select a desired CCD frame readout frequency;

compensating for a time delay between a pulse from the master clock corresponding to a fractional pixel position and the corresponding detected peak in the CCD output voltage.

19. The method of claim 13 where the steps of projecting and imaging a grid pattern also comprise the steps of:

pulsing the light source at a rate equal to a desired CCD frame rate;

selecting a short enough pulse width for said light source so that saccadic eye movement of an in-vivo semi-diffuse corneal target surface does not degrade measurement accuracy;

synchronizing CCD shutter action with the light source pulsing so as to capture all of the pulsing light while minimizing ambient light;

minimizing diffraction blurring caused by the projection system and mask.

20. A method for topography determination of a semi-diffuse surface comprising the steps of:

directing a plane polarized monochromatic pulsed through a mask to project a grid pattern on said surface;

placing a plane polarizing filter rotated at right angles to the plane of polarization of the monochromatic light source thereby blocking specular light while passing diffuse light emanating from said projected grid pattern;

imaging said pattern on a CCD of a video camera by means of an objective lens;

initiating a readout of pixels comprising the image on the CCD, said initiating also being the point in time of initiating a count of pulses from a master clock;

storing said count when a peak voltage out of the CCD corresponding to the readout of a light intensity peak occurring on a pixel or between two pixels is detected;

correlating said count with a two dimensional coordinate point on said CCD;

calculating the three dimensional topography of said surface by means of an algorithm that uses the fore knowledge of the point of origin and direction cosines of a first set of rays comprising the projected grid pattern, said algorithm using said two dimensional CCD coordinates to form a second set of rays, this second set of rays passing through a second point, said second point being the center of said objective lens, said second point and said two dimensional CCD coordinates forming a second set of direction cosines;

solving for the intersection points in three dimensional space, said intersection points being the desired topography.

* * * * *